United States Patent [19]

Weyenberg et al.

[11] Patent Number: 5,571,540
[45] Date of Patent: Nov. 5, 1996

[54] APPARATUS FOR CRIMPING, PLEATING AND FORMING A TIP ON A HOLLOW TUBE

[75] Inventors: Jeffrey M. Weyenberg, Appleton; Noel J. Rasmussen, Oshkosh; Richard R. Tews, Larsen, all of Wis.

[73] Assignee: Kimberly-Clark Corporation, Neenah, Wis.

[21] Appl. No.: 584,808

[22] Filed: Jan. 11, 1996

Related U.S. Application Data

[63] Continuation of Ser. No. 300,987, Sep. 6, 1994, abandoned.

[51] Int. Cl.$^6$ .................................................. B29C 57/10
[52] U.S. Cl. .......................... 425/343; 264/296; 425/393; 493/156; 493/308; 604/14
[58] Field of Search ....................................... 425/343, 392, 425/393; 264/296; 604/14; 493/156, 308

[56] References Cited

U.S. PATENT DOCUMENTS

| | | | |
|---|---|---|---|
| 1,181,965 | 5/1916 | Bohlman | 493/158 |
| 2,178,840 | 11/1939 | Lorenian | 604/200 |
| 2,298,752 | 10/1942 | Crockford | 604/11 |
| 2,403,042 | 7/1946 | Bogoslowsky | 425/393 |
| 2,639,646 | 5/1953 | Thompson et al. | 493/156 |
| 2,916,975 | 12/1959 | Gasior et al. | 493/109 |
| 3,078,025 | 2/1963 | Welshon | 229/400 |
| 3,087,390 | 4/1963 | Ruza | 425/393 |
| 3,141,595 | 7/1964 | Edwards | 229/400 |
| 3,164,314 | 1/1965 | Waycie | 229/400 |
| 3,203,611 | 8/1965 | Anderson et al. | 229/403 |
| 3,204,635 | 9/1965 | Voss et al. | 604/14 |
| 3,226,464 | 12/1965 | Saumsiegle et al. | 425/393 |
| 3,312,383 | 4/1967 | Shapiro et al. | 229/400 |
| 3,347,234 | 10/1967 | Voss | 604/14 |
| 3,433,225 | 3/1969 | Voss et al. | 604/14 |
| 3,475,786 | 11/1969 | Pearson | 425/393 |
| 3,572,339 | 3/1971 | Voss et al. | 604/15 |
| 3,575,169 | 4/1971 | Voss | 604/18 |
| 3,581,744 | 5/1971 | Voss | 604/14 |
| 3,676,543 | 7/1972 | Reinhold et al. | 264/296 |
| 3,696,812 | 10/1972 | Jaycox | 604/18 |
| 3,805,786 | 4/1974 | Bernardin et al. | 604/14 |
| 3,807,399 | 4/1974 | Morman et al. | 604/14 |

(List continued on next page.)

FOREIGN PATENT DOCUMENTS

| | | |
|---|---|---|
| 2095390 | 11/1993 | Canada . |
| 35-27595 | 10/1960 | Japan . |
| 1012217 | 12/1965 | United Kingdom . |
| 1484912 | 9/1977 | United Kingdom . |

*Primary Examiner*—James P. Mackey
*Attorney, Agent, or Firm*—Thomas J. Connelly

[57] ABSTRACT

An apparatus and method are disclosed for crimping, pleating and forming a tip on a hollow tube. The apparatus includes a first punch having a tubular section sized to receive the tube and having a configured tip with a plurality of elongated grooves formed therein. The first punch also contains a shoulder formed at an opposite end of the tubular section which acts as a stop for the tube. The first punch and tube are mateable with a first die. The first die includes a base having a plurality of blades extending axially outward therefrom. Each blade is designed to engage with one of the grooves formed on the first punch and causes the tip of the tube to be crimped therebetween. After an end of the tube has been crimped, it is transformed into a plurality of pleats and configured into a semi-spherically shaped tip having a central aperture formed therethrough. This is accomplished using a second punch having a tubular section sized to receive the tube. The second punch also has a semi-spherically shaped tip with a pin extending outward from the apex thereof and a shoulder formed at an opposite end of the tubular section which acts as a stop for the tube. The second punch and tube are mateable with a second die. The second die includes a base having a semi-spherical cavity formed therein with a central passageway formed at the bottom of the cavity. The cavity is sized to receive both the second punch and the tube while the passageway is sized to receive only the pin. The method of engaging the punches and dies to crimp, pleat and form one end of the tube is also described.

12 Claims, 5 Drawing Sheets

U.S. PATENT DOCUMENTS

| | | | |
|---|---|---|---|
| 4,104,013 | 8/1978 | Kelly et al. | 425/324.1 |
| 4,215,087 | 7/1980 | Mathison | 264/320 |
| 4,298,331 | 11/1981 | Mueller | 425/393 |
| 4,302,174 | 11/1981 | Hinzmann | 425/341 |
| 4,404,159 | 9/1983 | McFarlane | 425/393 |
| 4,406,607 | 9/1983 | Wildmoser | 425/393 |
| 4,412,833 | 11/1983 | Wiegner et al. | 604/14 |
| 4,453,925 | 6/1984 | Decker | 604/14 |
| 4,479,791 | 10/1984 | Sprague | 604/14 |
| 4,508,531 | 4/1985 | Whitehead | 604/14 |
| 4,551,292 | 11/1985 | Fletcher et al. | 425/393 |
| 4,551,293 | 11/1985 | Diehl, Jr. et al. | 425/393 |
| 4,650,459 | 3/1987 | Sheldon | 604/15 |
| 4,661,300 | 4/1987 | Daugherty | 425/393 |
| 4,778,374 | 10/1988 | Takahashi et al. | 425/343 |
| 4,846,802 | 7/1989 | Sanders, III | 604/15 |
| 5,184,995 | 2/1993 | Kuchenbecker | 493/79 |
| 5,279,541 | 1/1994 | Frayman et al. | 604/14 |
| 5,290,501 | 3/1994 | Klesius | 264/322 |

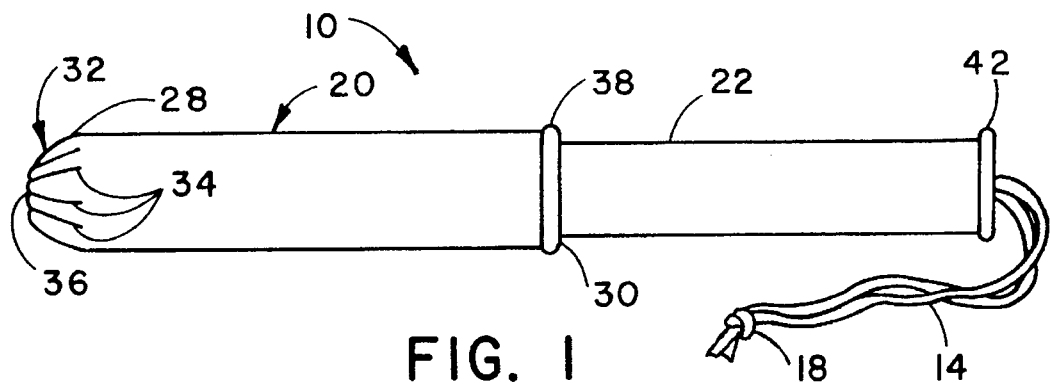
FIG. 1
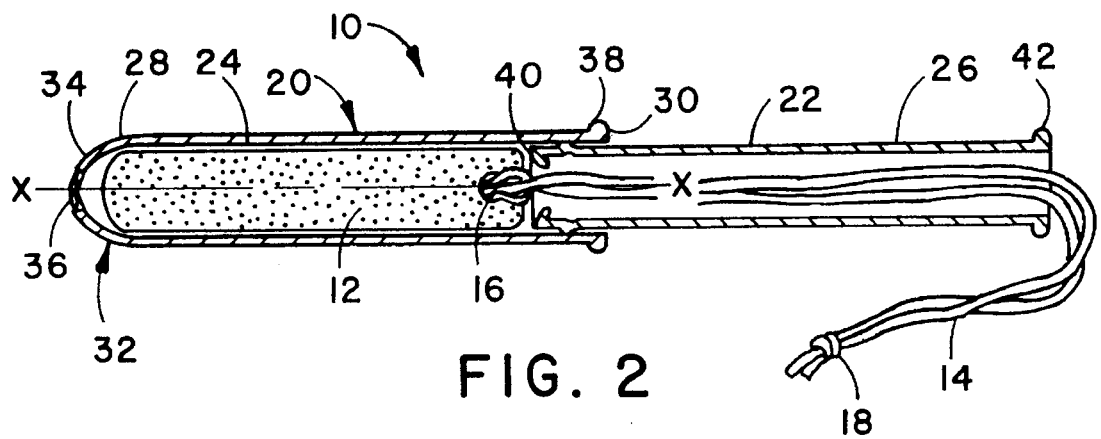
FIG. 2
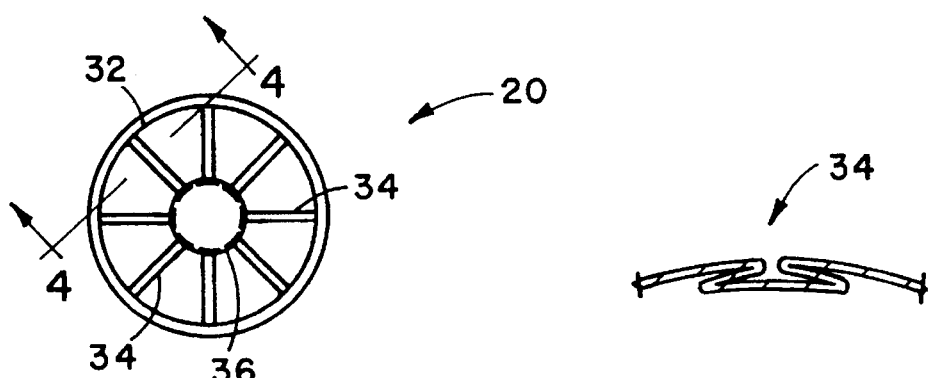
FIG. 3
FIG. 4

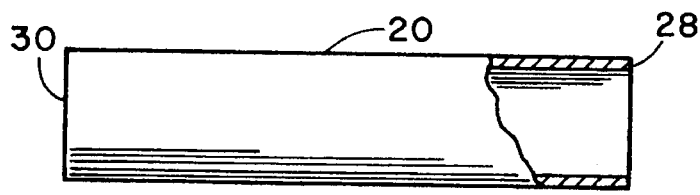
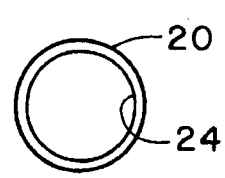
FIG. 5     FIG. 6
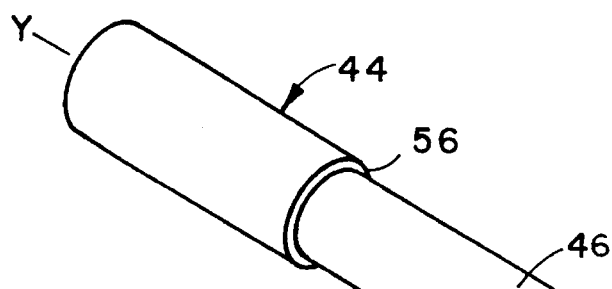
FIG. 7
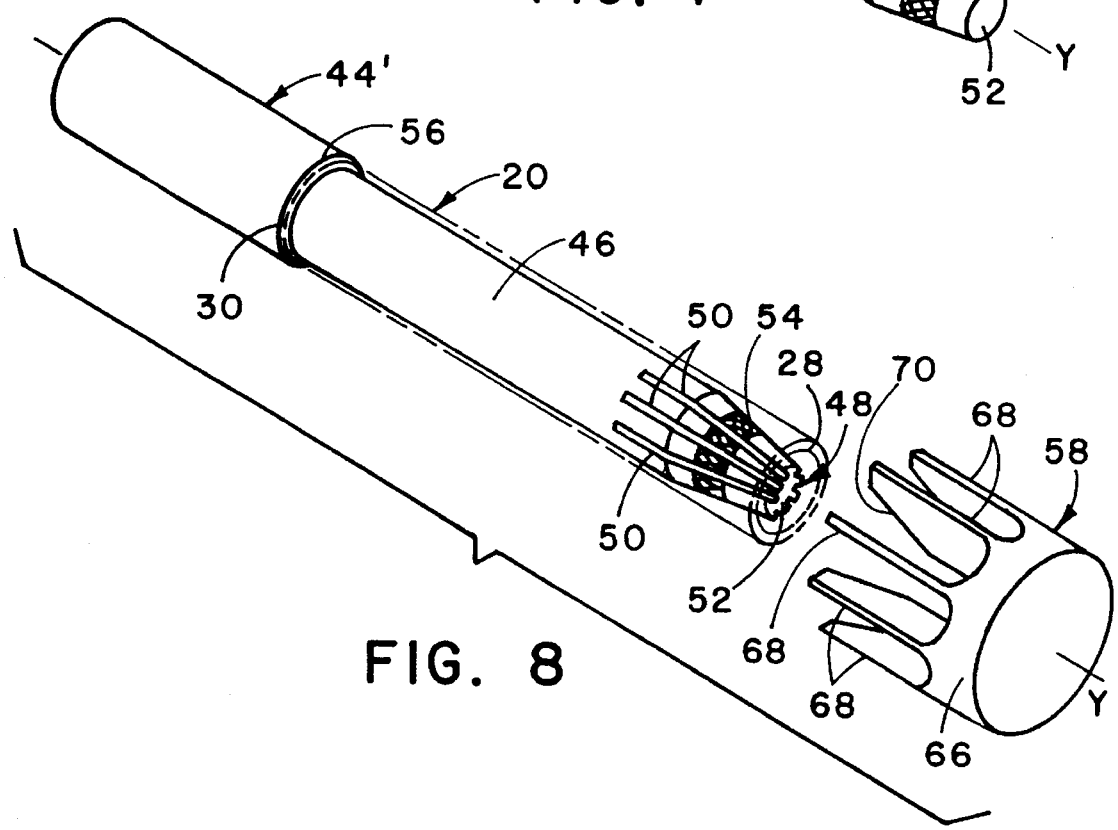
FIG. 8

APPARATUS FOR CRIMPING, PLEATING AND FORMING A TIP ON A HOLLOW TUBE

This application is a continuation of application Ser. No. 08/300,987 entitled "APPARATUS FOR CRIMPING, PLEATING AND FORMING A TIP ON A HOLLOW TUBE" and filed in the U.S. Patent and Trademark Office on Sep. 6, 1994 now abandoned. The entirety of this application is hereby incorporated by reference.

FIELD OF THE INVENTION

This invention relates to an apparatus and method for crimping, pleating and forming a tip on a hollow tube. More specifically, this invention relates to crimping, pleating and forming an insertion tip in an end of a paper tampon applicator.

BACKGROUND OF THE INVENTION

Tampon applicators which include a pair of telescoping tubes are well known in the art. In such applicators, an absorbent tampon is positioned in the forward end of a relatively large diameter outer tube. A smaller diameter inner tube is telescopically retained within the rear end of the outer tube such that the forward end of the inner tube abuts the rear end of the absorbent tampon. In the most preferred designs, the forward end of the outer tube, which is inserted into a woman's vagina prior to tampon injection, includes a smooth and rounded insertion tip to enhance user comfort. As the user pushes the inner tube against the rear end of the tampon, the tampon is moved forward causing the insertion tip to open and expand to a sufficient size to allow the tampon to be expelled from the outer tube. Following expulsion of the tampon, the insertion tip may radially contract toward its original closed position so as to permit the tampon applicator to be comfortably withdrawn from the body cavity.

Such tampon applicators are conventionally manufactured from either paper or plastic. As used herein, the term "paper" refers to applicators constructed out of paper, paperboard, cardboard or combinations thereof, including laminates containing one or more layers of thermoplastic films and/or plastics. Paper applicators are generally spirally wound, convolutely wound or longitudinally seamed into a cylindrical shape while plastic applicators are typically injection molded. Because of environmental concerns, paper applicators which are water degradable and/or water dispersible, are increasingly preferred.

The insertion tip on the outer tube of a tampon applicator can be rounded, tapered or frusto-conical in configuration and can contain a plurality of petals separated by slots. The petals are designed to expand radially outward as the tampon is expelled from the outer tube. Such petals are taught in U.S. Pat. No. 3,204,635 issued to Voss et al. and U.S. Pat. No. 4,508,531 issued to Whitehead. however, such petals have a tendency, as they open and close, to pinch the vaginal tissue and cause discomfort. In order to avoid this problem, some manufacturers have elected to completely enclose the forward end of the outer tube and use perforations or weakened lines as a means for opening the tip. Still other manufacturers have used a plurality of pleats which are capable of expanding radially outward as the tampon is expelled from the outer tube.

Now an apparatus and method for crimping, pleating and forming an insertion tip on the end of a paper tampon applicator has been invented which provides a central aperture formed through the insertion tip. The central aperture allows the pleats to open with a minimum amount of expulsion force and provides a visual means for the consumer to verify that the applicator does contain an absorbent tampon.

SUMMARY OF THE INVENTION

Briefly, this invention relates to an apparatus and method for crimping, pleating and forming a tip on a hollow tube. The apparatus includes a first punch having a tubular section sized to receive the tube and having a configured tip with a plurality of elongated grooves formed therein. The first punch also contains a shoulder formed at an opposite end of the tubular section which acts as a stop for the tube. The first punch and tube are mateable with a first die. The first die includes a base having a plurality of blades extending axially outward therefrom. Each blade is designed to engage with one of the grooves formed on the first punch and causes the tip of the tube to be crimped therebetween. After an end of the tube has been crimped, it is transformed into a plurality of pleats and configured into a semi-spherical configuration having a central aperture formed therethrough. This is accomplished using a second punch having a tubular section sized to receive the tube. The second punch also has a semi-spherically shaped tip with a pin extending outward from the apex thereof and a shoulder formed at an opposite end of the tubular section which acts as a stop for the tube. The second punch and tube are mateable with a second die. The second die includes a base having a semi-spherical cavity formed therein with a central opening formed at the bottom of the cavity. The cavity is sized to receive the second punch and the tube, and the opening is sized to receive only the pin. The method of engaging the punches and dies to crimp, pleat and form one end of the tube is also described.

The general object of this invention is to provide an apparatus and method for crimping, pleating and forming a tip on a hollow tube. A more specific object of this invention is to provide an apparatus and method for crimping, pleating and forming an insertion tip on an end of a paper tampon applicator.

Another object of this invention is to provide an apparatus for crimping, pleating and forming the insertion end of a paper tampon applicator into a semi-spherical configuration having a central aperture formed therethrough.

A further object of this invention is to provide an apparatus which is simple to build and easy to operate.

Still another object of this invention is to provide a method for crimping, pleating and forming the insertion end of a tampon applicator at high speeds.

Still further, an object of this invention is to provide a simple and economical method of crimping, pleating and forming the insertion end of a tampon applicator.

Other objects and advantages of the present invention will become more apparent to those skilled in the art in view of the following description and the accompanying drawings.

BRIEF DESCRIPTION OF THE DRAWINGS

FIG. 1 is a perspective view of a paper tampon applicator having an inner tube and an outer tube.

FIG. 2 is a cross-sectional view of a tampon applicator shown in FIG. 1.

FIG. 3 is a left end view of the tampon applicator shown in FIG. 1 depicting eight pleats.

FIG. 4 is a schematic view of a pleat taken along line 4—4 of FIG. 3 depicting the shape and thickness of a pleat.

FIG. 5 is a side elevational view of the outer tube before the insertion tip is formed.

FIG. 6 is a right end view of the outer tube shown in FIG. 5.

FIG. 7 is a perspective view of a first punch.

FIG. 8 is a perspective view of a first punch having a plurality of grooves formed in the tip and showing the first punch being mateable with a first die.

DETAILED DESCRIPTION OF THE PREFERRED EMBODIMENTS

Figure 9:
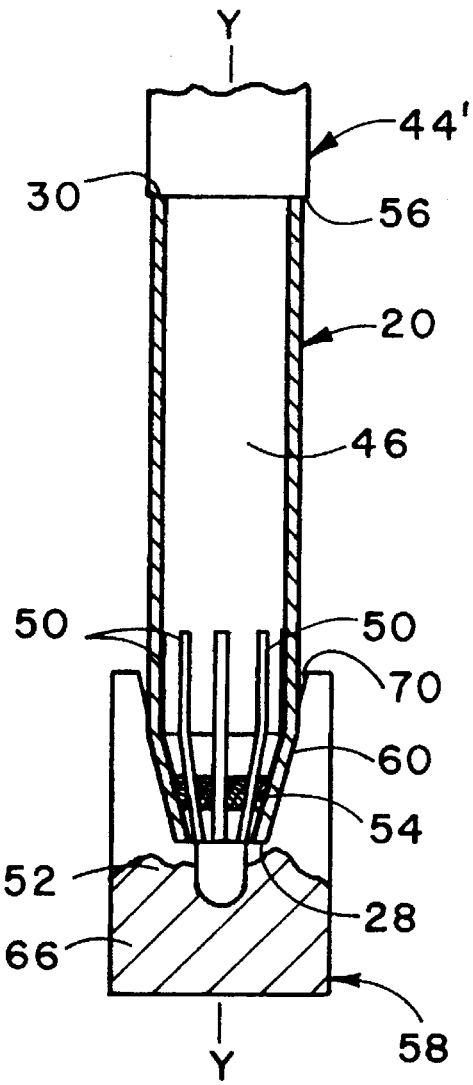
FIG. 9 is a partial section view showing the first punch and outer tube mating with the first die.

Referring to FIGS. 1–3, a tampon applicator 10 is shown which is designed to house an absorbent tampon 12 and provide a comfortable means of inserting the tampon 12 into a woman's vagina. A tampon is an absorbent member primarily designed to be worn by a woman during her menstrual period to absorb menses, blood and other body fluid. The tampon 12 can be made from natural or synthetic fibers including cellulose fibers such as cotton or rayon, or artificial fibers such as polyester, polypropylene, nylon or blends thereof. Other types of fibers may also be used, such as cellulose sponge or a sponge formed from elastomeric materials. A blend of cotton and rayon fibers works well.

The tampon 12 is normally compressed into the form of a cylinder and can have a blunt, rounded or shaped forward end. The tampon 12 commonly has a withdrawal string 14 fastened to an end thereof which serves as a means for withdrawing the soiled tampon from the woman's vagina. The withdrawal string 14 is permanently affixed to the tampon 12, for example, by looping it through an aperture 16 formed transversely through the tampon 12. In addition, the withdrawal string 14 can have a knot 18 formed at it's free end to assure that the string 14 will not separate from the tampon 12.

The tampon applicator 10 includes an outer tube 20 and an inner tube 22. The outer tube 20 is preferably in the form of a spirally wound, convolutely wound or longitudinally seamed, hollow tube which is formed from paper, paperboard, cardboard or a combination thereof. The inner tube 22 can be formed from the same material as the outer tube 20, or alternatively, be made of a different material. The inner tube 22 should have a constant external diameter so as to easily slide within the inner diameter of the outer tube 20. It is also possible to construct the inner tube 22 as a solid stick, or use some other unique shape, which attaches directly to the tampon 12.

Both the outer tube 20 and the inner tube 22 are fairly rigid and commonly have a diameter of about 10 mm to about 20 mm, with the inner tube 22 being slightly smaller in diameter than the outer tube 20. The outer tube 20 has a wall 24 with a predetermined thickness of about 0.2 mm to about 0.6 mm. The inner tube has a wall 26 which is slightly thinner. The walls 24 and 26 can be constructed from a single ply of material or be formed from two or more plies which are bonded together to form a laminate. The use of two or more plies or layers is preferred for it enables the manufacturer to use certain material in the various layers which can enhance the performance of the tampon applicator 10. When two or more layers are utilized, all the layers can be spirally wound, convolutely wound or longitudinally seamed to form an elongated cylinder. The exterior surface of the wall 24 can be constructed using a smooth thin layer of material to facilitate insertion of the first member 20 into a woman's vagina.

The layers forming the walls 24 and 26 can be held together by an adhesive, such as glue, or by heat, pressure, ultrasonics, etc. The adhesive can be either water-soluble or water-insoluble. A water-soluble adhesive is preferred for environmental reasons in that the tubes 20 and 22 will quickly break apart when immersed in water. Such immersion will occur should the tubes 20 and 22 be disposed of by flushing them down a toilet. Exposure of the tubes 20 and 22 to a municipal's waste treatment plant wherein soaking in water, interaction with chemicals and agitation all occur, will cause the tubes 20 and 22 to break apart in a relatively short period of time.

The outer tube 20 is sized and configured to house the absorbent tampon 12 and the inner tube 22 is sized and configured to push the tampon 12 out of the outer tube 20. The outer tube 20 can be a straight, elongated cylindrical tube formed on a central longitudinal axis X—X. It is also possible to form the outer tube 20 into an arcuate shape. The arcuate or curved shape can assist in providing comfort when inserting the outer tube 20 into a woman's vagina. The inner tube 22 should be configured to telescopically slide in the outer tube 20. With a curved tampon applicator, it is possible to employ a curved tampon which again may be more comfortable for some women to use since the shape of the tampon may better fit the curvature of a woman's vagina.

The outer tube 20 has first and second spaced apart ends 28 and 30, respectively. The outer tube 20 can also have either a constant outer diameter or a stepped outer profile. Preferably, the outer tube 20 will have an essentially constant diameter over a major portion of it's length. Integrally formed on the first end 28 of the outer tube 20 and extending outwardly therefrom is an insertion tip 32. The insertion tip 32 is designed to facilitate insertion of the outer tube 20 into a woman's vagina in a comfortable manner. The insertion tip 32 contains a number of pleats 34 and has a semi-spherical configuration with a diameter which is approximately equal to the outside diameter of the outer tube 20. The pleats 34 can be uniformly spaced apart or they can be randomly arranged. The insertion tip 32 can have the same thickness as the outer tube 20 or be made thinner or thicker, if desired.

An aperture 36 is formed in the center of the semi-spherical shaped insertion tip 32 and is coaxially aligned with the longitudinal axis X—X. The aperture 36 can have a diameter of at least about 1.5 mm, preferably between about 1.5 to about 5.0 mm, and more preferably, between about 3.0 to about 3.5 mm. Another way of sizing the diameter of the aperture 36 is to make it less than about 30% of the diameter of the outer tube 20, preferably, between about 10% to about 30%, and most preferably, less than about 20% of the diameter of the outer tube 20. It should be noted that although the aperture 36 is described as a circle, it is possible to form the aperture 36 in other shapes such as a polygon, a square, a pentagon, a hexagon, an octagon, etc. The aperture 36 should extend entirely through the insertion tip 32. The purpose of the aperture 36 in the end of the insertion tip 32 is to facilitate the subsequent unfolding of the pleats 34 during use. The aperture 36 also assures that the pleats 34 will symmetrically open about the longitudinal axis X—X of the outer tube 20. A further benefit of the aperture 36 is that it provides a visual means for the user to inspect the tampon applicator 10 and assure herself that a tampon 12 is present in the outer tube 20.

With the aperture 36 being small, less of the absorbent tampon 12 is exposed to the vaginal tissue when the tampon applicator 10 is inserted into the woman's vagina. Since a tampon 12 is normally dry and consists of a plurality of absorbent fibers, it can cause abrasion against the walls of a woman's vagina as it is being inserted. By reducing the amount of surface area of the tampon 12 which is exposed to the vaginal tissue, one can decrease the discomfort during the insertion process. In addition, since a majority of the insertion tip 32 is closed, the frictional force between the exterior surface 26 of the outer tube 20 and the walls of the vagina is reduced. Furthermore, the small diameter of the aperture 36 also decreases the possibility of trapping or pinching vaginal tissue therein.

Referring to FIGS. 3 and 4, the insertion tip 32 is shown having a plurality of pleats 34 which can radially open such that the insertion tip 32 has a diameter which is approximately equal to or larger than the diameter of the outer tube 20. The term "pleat" as used herein refers to material which is folded upon itself, for example, by doubling the material upon itself and then pressing it into place. A representative view of a pleat 34 is depicted in FIG. 4. Either an even or an odd number of pleats 34 can be present and the pleats 34 can be equally spaced apart or they can be uniformly or randomly arranged. For ease of manufacturing, it is preferred that the pleats 34 be equally spaced relative to one another. Each pleat 34 is formed by doubling the material upon itself and then pressing or adhering the material into place. Although eight equally spaced apart pleats 34 are shown in FIG. 3, it is possible to utilize various numbers of pleats 34. The number of pleats 34 can vary from between three to about thirty-two pleats, preferably between five to sixteen pleats, and most preferably, eight pleats.

Referring again to FIGS. 1 and 2, the outer tube 20 can have a fingergrip ring 38 located approximate the second end 30. The fingergrip ring 38 can be integrally formed from the material from which the outer tube 20 is constructed or it can be a separate member which is secured in place by an adhesive or some other type of attachment mechanism. The fingergrip ring 38 functions to provide a means for the user to grip the outer tube 20 and hold it between her thumb and middle finger. The user can then position her forefinger on the free end of the inner tube 22 and orient the outer tube 20 relative to her vagina while she pushes the inner tube 22 into the outer tube 20.

The inner tube 22 can have an inwardly directed flange 40 formed at its forward end which provides an enlarged surface for contacting the rear end of the tampon 12. The inner tube 22 can also have a radial, outwardly extending ring 42 formed adjacent to the outer or free end of the inner tube 22 which provides an enlarged surface onto which the user's forefinger can rest. The ring 42 thereby functions as a seat for the forefinger and facilitates movement of the inner tube 22 into the outer tube 20.

The inner tube 22 functions by being telescopically movable relative to the outer tube 20. As the inner tube 22 is pushed into the outer tube 20, the tampon 12 is forced forward against the pleats 34. The contact by the tampon 12 causes the pleats 34 to radially open to a diameter which is sufficient to allow the tampon 12 to be expelled from the outer tube 20. With the tampon 12 properly positioned in the woman's vagina, the tampon applicator 10 is withdrawn and properly discarded.

APPARATUS

The outer tube 20 can have the insertion tip 32 formed into the desired semi-spherical configuration with the central aperture 36 by using the apparatus described below.

Referring to FIGS. 5 and 6, the outer tube 20 is shown before the insertion tip 32 is formed. At this stage, the outer tube 20 has an essentially constant inside diameter and the wall 24 has a constant thickness.

Referring to FIGS. 7 and 8, a first punch 44 is shown having a tubular section 46 which is sized and configured to receive the outer tube 20. In other words, the outer tube 20 must be able to slide onto the tubular section 46 with only a small amount of clearance therebetween. The first punch 44 has a tip 48. The tip 48 can be smooth or void of any grooves as shown in FIG. 7. Alternatively, the first punch 44' can have a configured tip 48 with a plurality of elongated grooves 50 formed therein, as is depicted in FIG. 8. When the grooves 50 are present, there should be at least four grooves 50, preferably between eight to twelve grooves 50, with eight grooves 50 being most preferred. The purpose of the grooves 50 will be explained shortly.

The tip 48 can be formed into a frusto-conical shape having a blunt end 52. Other shapes can also be utilized if desired. At least a portion of the exterior surface of the tip 48 can be knurled 54 to provide a frictional surface between the tip 48 and the inner surface of the outer tube 20 as the insertion tip 32 is being formed. A medium knurl 54 will provide an adequate frictional surface for the crimping operation. The first punch 44 or 44' also has a shoulder 56 formed at an opposite end of the tubular section 46 which acts as a stop for the outer tube 20. It should be noted that the length of the tubular section 46 is sized to conform closely to the length of the outer tube 20. A typical outer tube 20 will have a length of between about 2 inches to about 4 inches (about 50.8 mm to about 101.6 mm), preferably about 3 inches to about 3.5 inches (about 76.2 mm to about 88.9 mm), most preferably, at least about 3.12 inches (about 79.2 mm). The tubular section 46 should have a length which is equal to or slightly greater than the initial length of the outer tube 20 as shown in FIG. 5. The first end 28 of the tube 20 can be aligned approximately flush with the tip 48 when the tube 20 is positioned on the tubular section 46. However, an extra length of about 0.06 inches (about 1.5 mm) on the tubular section 46 of the first punch 44 or 44' is advantageous for permitting the first punch 44 or 44' to mate with a first die 58.

Referring to FIGS. 8 and 9, the first punch 44' is shown with the outer tube 20 slid onto the tubular section 46 such that the second end 30 of the outer tube 20 abuts the shoulder 56 and is mateable with the first die 58. The axial engagement of both the first punch 44' and the outer tube 20 with the first die 58 enables the tip 32 of the outer tube 20 to be crimped. The term "crimped" as used herein refers to pressing or pinching the material forming the insertion tip 32 into small, regular folds or ridges with troughs therebetween.

Figure 10:
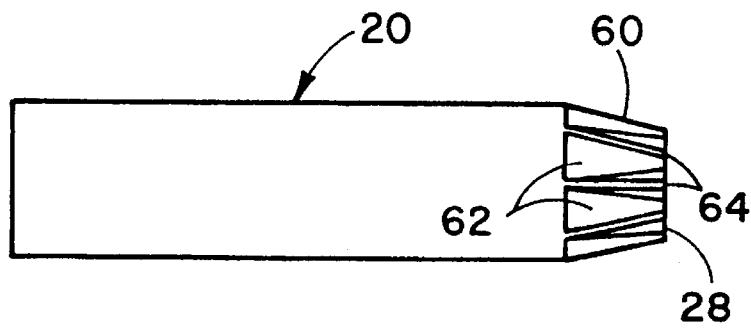
FIG. 10 is a side elevational view of the outer tube showing the insertion tip after undergoing crimping.
Figure 11:
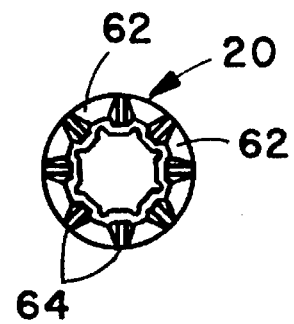
FIG. 11 is a right end view of the outer tube shown in FIG. 10.

Referring to FIGS. 10 and 11, the crimped tip 60 consists of a plurality of ridges 62 and troughs 64 formed about the circumference of the first end 28 of the outer tube 20. The troughs 64 are the deepest adjacent the first end 28 and become shallower as the troughs move away from the first end 28. The ridges 62 are formed on a circle having a smaller diameter adjacent the first end 28 and expand outward as the ridges 62 move away from the first end 28.

Referring again to FIGS. 8 and 9, the crimped tip 60 is formed by the engagement of the first punch 44 or 44' with the first die 58. The first die 58 includes a base 66 having a plurality of blades 68 extending axially outward therefrom. There should be at least four blades 68, preferably, between eight to twelve blades, with eight blades being the most preferred. For best results with hard board papers, each groove 50 formed in the first punch 44' should align with a blade 68 formed in the first die 58. Either an even number or an odd number of blades 68 can be utilized. An even number of blades 68 are easier to machine and the first die 58 will then have a symmetrical shape, which is also advantageous. For example, symmetrically shaped dies can be measured across their tips to determine their size.

The blades 68 can range from about 0.5 inches (about 12.7 mm) to about 2 inches (about 50.8 mm) in length. A length of approximately 1 inch (25.4 mm) is sufficient. The blades 68 have an angled or tapered inner surface 70 which enables then to mate with the smooth tip 48 formed on the first punch 44 or mate with and axially enter a corresponding groove 50 formed in the first punch 44'. The angle can vary depending upon the taper on the smooth tip 48 or depending on the angle at which each corresponding groove 50 is formed. The angle on each blade 68 can be equal to or different from the angle formed on the smooth tip 48 and can also be equal to or different from the angle to which each groove 50 is machined. When the grooves 50 are present, each groove 50 should be sized to be larger than the corresponding blade 68 so that the thickness of wall 24 of the outer tube 20 can also be received into the grooves 50. Each blade 68 is machined to an angle which is different from the angle to which the bottom of the grooves 50 have been machined to. When the first punch 44' is fully inserted into the first die 58, the angled surfaces 70 of each blade 68 is spaced apart from the bottom of each corresponding groove 50. This clearance permits the wall thickness of the outer tube 20 to be sandwiched therebetween and provides the undulating surface which is the crimp 60 shown in FIG. 11. The angle that each groove 50 and each blade 68 is formed at can vary. The grooves 50 and the blades 68 can be formed at identical angles relative to a longitudinal central axis Y—Y of the first punch 44' and the first die 58, or they can be formed at different angles relative to one another. For outer tubes 20 formed from hard paperboard, good quality pleats 34 can be formed using the first punch 44 with the smooth tip 48 mating with the first die 58. For softer paperboard, it is advantageous to machine an angle of about 20° to the Y—Y axis in the first die 58 and to machine an angle of about 15° to the Y—Y axis in the first punch 44'.

Referring to FIG. 9, one can see the position of the outer tube 20 on the first punch 44' while the first end 28 is crimped. The knurled surface 54 serves to prevent the outer tube 20 from moving toward the shoulder 56 when the first punch 44' engages the first die 58. It has been found that the force exerted on the outer tube 20 increases as the first punch 44 or 44' engages deeper and deeper into the first die 58. When the knurled surface 54 is not present, this force can drive the outer tube 20 up against the shoulder 56 and cause the second end 30 of the outer tube 20 to become wrinkled and radially enlarged. Such a feature is not aesthetically pleasing and must be avoided.

After the outer tube 20 has a crimped tip 60 formed on the first end 28 thereof, the first punch 44 or 44' and the first die 58 are separated and the outer tube 20 is removed.

Figure 12:
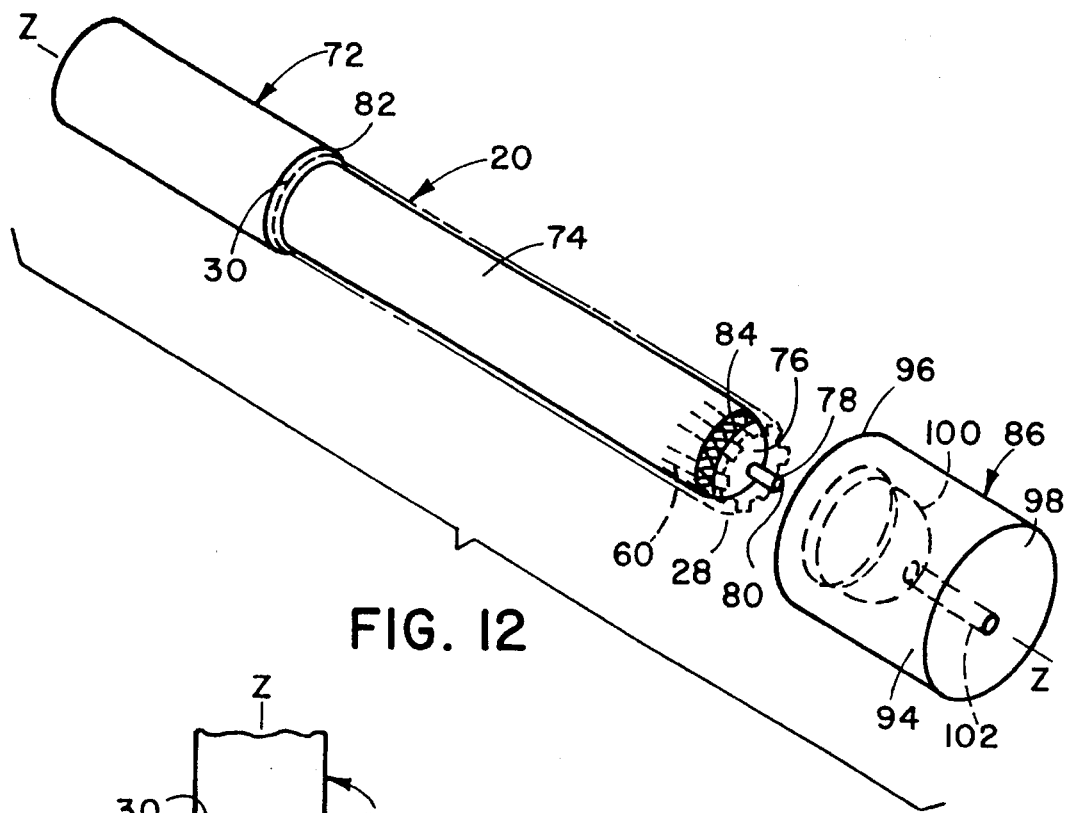
FIG. 12 is a perspective view of the second punch and the second die with the outer tube shown in phantom.
Figure 13:
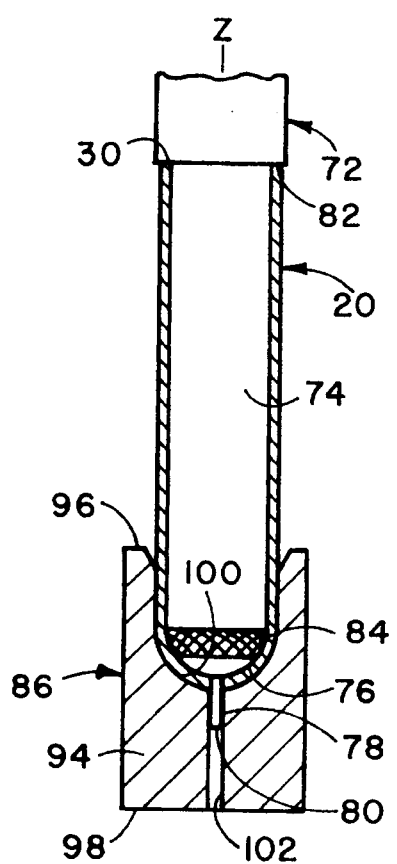
FIG. 13 is a partial section view showing the second punch and outer tube mating with the second die.

Referring to FIGS. 12 and 13, the outer tube 20 is then subjected to a second operation wherein the crimped tip 60 is pleated and pressed into a semi-spherical configuration. This is accomplished by using a second punch 72 having a tubular section 74 which is sized to receive the outer tube 20. The second punch 72 has a semi-spherically shaped tip 76 with a pin 78 extending outward from the apex of the tip 76. The pin 78 has a distal or free end 80. The second punch 72 also contains a shoulder 82 formed at an opposite end of the tubular section 74 which acts as a stop for the outer tube 20. It should be noted that the length of the tubular section 74 is sized to conform closely to the length of the outer tube 20. The second punch 72 is designed to have the outer tube 20 slid over the tubular section 74 until the second end 30 of the outer tube 20 abuts against the shoulder 82. In this position, the crimped tip 60 formed on the first end 28 of the outer tube 20 should extend about 0.06 inches to about 0.12 inches (about 1.5 mm to about 3.0 mm) beyond the apex of the semi-spherically shaped tip 76. The free end 80 of the pin 78, however, will extend beyond the crimped end 60 by at least 0.06 inches (1.5 mm), and preferably more.

At least a portion of the semi-spherically shaped tip 76 can be knurled 84 to provide a frictional surface between the tip 76 and the inner surface of the outer tube 20 as the insertion tip 32 is being formed. A medium knurl 84 will provide an adequate frictional surface for the pleating and forming operation. The knurled surface 84 serves to prevent the outer tube 20 from moving toward the shoulder 82 of the second punch 72.

The pin 78 can have a length of at least 0.06 inches (1.5 mm) but is preferably longer. The pin 78 should have a diameter of at least 0.062 inches (1.5 mm), preferably at least 0.125 inches (3.1 mm), and can be larger if desired. The cross-section of the pin 78 is preferably circular but could be of a different configuration if desired. A circular cross-section is preferred for it forms an opening with a circular periphery. A circular opening is aesthetically pleasing to the eye and since one of the purposes of the aperture 36 is to allow the consumer to see if a tampon 12 is present in the tampon applicator 10, the aperture could be circular. The pin 78 is shown having an essentially constant outside diameter. However, it is possible to form the pin 78 such that it tapers down in diameter from a larger diameter located adjacent to the point of attachment to the apex of the semi-spherical tip 76 to a smaller diameter adjacent the free end 80.

Figures 14, 15:
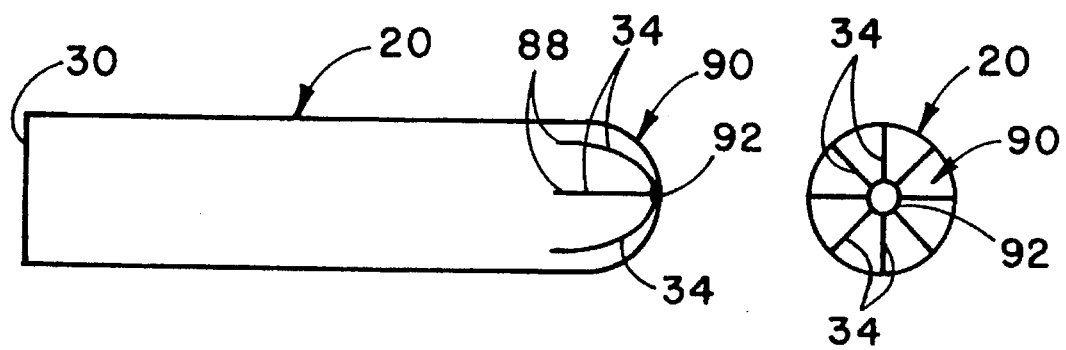
FIG. 14 is a side elevational view of the outer tube showing the insertion tip after undergoing crimping, pleating and forming into a semi-spherical configuration.
FIG. 15 is a right end view of the outer tube shown in FIG. 14.
Figure 16:
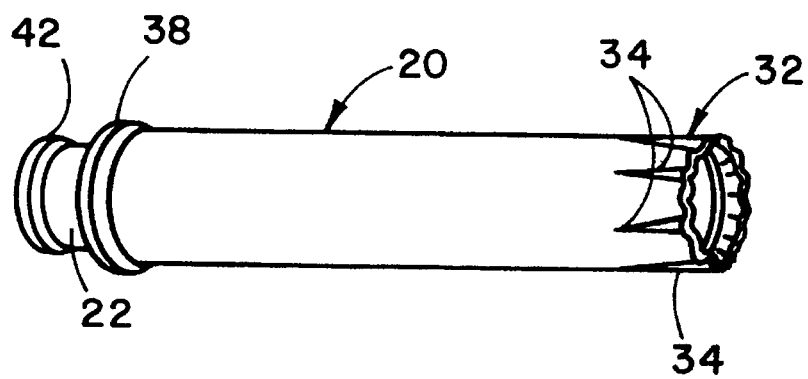
FIG. 16 is a perspective view of the tampon applicator showing the pleats in an open arrangement after the tampon has been expelled by the inner tube.

The second punch 72 is sized and configured to engage with a second die 86 so as to transform the crimped tip 60 of the outer tube 20 into a plurality of pleats 34 and form the pleats 34 into a semi-spherically shaped tip 90, see FIGS. 14 and 15. The pleats 34 can be uniformly or randomly spaced apart and can have a dovetail-like appearance. The length of each pleat 34 should be aligned approximately straight with or parallel to the longitudinal axis of the tube 20 versus being undulating or curved. A straight pleat normally requires a lesser amount of force to open. The pleats 34 should terminate at a point 88 which is approximately tangent to the point where the semi-spherically shaped tip 90 joins to the exterior surface of the outer tube 20. The semi-spherically shaped tip 90 will have a central aperture 92 formed therethrough because of the presence of the pin 78. The aperture 92 allows the consumer to visually inspect the tampon applicator 10 to see if a tampon 12 is present. The aperture 92 can vary with the diameter of the tube 20 but should not be so large that it would allow a woman to feel it as she inserts the tampon 12 into her vagina. If the aperture 92 is too large, it could cause discomfort as the woman inserts the tampon applicator 10 into her vagina.

Referring again to FIGS. 12 and 13, the second die 86 includes a base 94 having a first end 96 and a second end 98. A semi-spherically shaped cavity 100 formed in the base 94 adjacent to the first end 96. The semi-spherically shaped cavity 100 is sized to receive the semi-spherically shaped tip 76 formed on the outer tube 20 as well as the wall thickness of the outer tube 20. This difference in size will allow the insertion tip 32 to be formed on the first end 28 of the outer tube 20. The surface of the cavity 100 is preferably polished to improve the appearance of the finished semi-spherically shaped tip 76 and to facilitate removal of the finished tube 20 from the second die 86. The polished surface can have a "surface roughness average" value of between about 4 micro inches to about 16 micro inches.

The base 94 also has a central passageway 102 formed therein which is axially aligned along a longitudinal central axis Z—Z. The passageway 102 extends from the bottom of the cavity 100 to the second end 98. If desired, the passageway 102 can be a closed passageway which terminates short of the second end 98. The passageway 102 is sized and configured to receive only the pin 78. The outside diameter of the pin 78 should be slightly smaller than the inside diameter of the passageway 102. The relationship between the mating second punch 72, the outer tube 20 and the second die 86 is clearly shown in FIG. 13.

It should be noted that both the length and diameter of commercially available tampons do vary and therefore the tampon applicator 10 should be manufactured in a variety of sizes. Tampons can vary in length from about 1 inch to about 3 inches (about 25.4 mm to about 76.2 mm) but preferably are about 2 inches (about 50.8 mm) in length. The tampon diameter will also vary from about 0.25 inches to about 0.75 inches (about 6.4 mm to about 19.0 mm). In addition, the material from which the tampon 12 is constructed, the smoothness of the internal surface of the outer tube 20, the shape of the inner tube 22, etc. all contribute to establish a needed expulsion force to open and expel the tampon 12. This force should range from between about 250 grams to about 1,500 grams, preferably less than about 1,200 grams, and most preferably, less than about 1,000 grams. A lower force value is preferred for it assures that the tampon applicator 10 will be less susceptible to being bent or deformed as the tampon 12 is expelled. A bent applicator could cause the tampon to be inserted incorrectly. A lower force value also makes the tampon applicator 10 easier to use. The size of the aperture 92 will also affect the amount of force needed to open the pleats 34. Typically, the larger the diameter of the aperture 92, the lower the force required to open the pleats 34.

METHOD

The method of crimping, pleating and forming a semi-spherically shaped tip 90 on a hollow tube 20 is as follows, using the above-identified punches 44, 44' and 72, and dies 58 and 86. The above identified punches 44, 44' and 72, and dies 58 and 86 can be manually or automatically engaged and disengaged to form the insertion tip 32 on the outer tube 20. It is contemplated that the punches 44, 44' and 72, and the dies 58 and 86 will be actuated at sufficient speeds to crimp, pleat and form in excess of 100, preferably in excess of 300, and most preferably, more than 500 outer tubes per minute.

The method involves sliding the hollow tube 20 onto the first punch 44 or 44' until one end 30 of the tube 20 contacts the shoulder 56. The first punch 44 or 44' and the tube 20 are moved into engagement with the first die 58 and a plurality of crimps are formed on the opposite end 28 of the tube 20. The plurality of crimps form the crimped end 60. The first punch 44 or 44' is then disengaged from the first die 58 and the tube 20 having the crimped end 60 is removed from the first punch 44 or 44'. The tube 20 is then slid onto the second punch 72 until the non-crimped end 30 of the tube 20 contacts the shoulder 82. The second punch 72 and the tube 20 are brought into engagement with the second die 86 thereby allowing the axially extending pin 78 to enter the passageway 102. The mating of the second punch 72 with the second die 86 transforms the crimped end 60 of the tube 20 into a plurality of pleats 34 and forms the pleats 34 into a semi-spherically shaped tip 90 having a central aperture 92 formed therethrough. Once the tip 90 is formed, the second punch 72 is disengaged from the second die 86 and the outer tube 20 is removed from the second punch 72.

While the invention has been described in conjunction with a number of specific embodiments, it is to be understood that many alternatives, modifications and variations will be apparent to those skilled in the art in light of the aforegoing description. Accordingly, this invention is intended to embrace all such alternatives, modifications and variations which fall within the spirit and scope of the appended claims.

We claim:

1. An apparatus for crimping, pleating and forming a tip on a hollow tube, said apparatus comprising:

a) a first punch having a tubular section sized to receive said tube and a shoulder formed at one end of said tubular section which acts as a stop for said tube, and said first punch further having a smooth tip void of any elongated grooves;

b) a first die mateable with said first punch and tube to crimp an end of said tube, said first die including a base having a plurality of blades extending axially outward therefrom, each of said blades capable of engaging said tube and crimping the tip of said tube positioned between said first die and said first punch;

c) a second punch having a tubular section sized to receive said tube and having a semi-spherically shaped tip with a pin extending outward from the apex thereof, and said second punch further having a shoulder formed at one end of said tubular section thereof which acts as a stop for said tube; and d) a second die mateable with said second punch to transform said crimped end of said tube into a plurality of pleats and form said pleats into a semi-spherically shaped tip having a central aperture formed therethrough, said second die including a base having a semi-spherical cavity formed therein with a central passageway formed at the bottom of said cavity, said cavity being sized to receive both said second punch and said tube and said passageway being sized to receive only said pin.

2. The apparatus of claim 1 wherein said pin has a circular cross-sectional configuration.

3. An apparatus for crimping, pleating and forming a tip on a hollow tube, said apparatus comprising:

a) a first punch having a tubular section sized to receive said tube and a shoulder formed at one end of said tubular section which acts as a stop for said tube, and said first punch further having a smooth tip void of any elongated grooves;

b) a first die mateable with said first punch and tube to crimp an end of said tube, said first die including a base having a plurality of blades extending axially outward therefrom, each of said blades capable of engaging said tube and crimping the tip of said tube positioned between said first die and said first punch;

c) a second punch having a tubular section sized to receive said tube and having a semi-spherically shaped tip with a pin extending outward from the apex thereof, said pin having a diameter of at least 0.125 inches, and said second punch further having a shoulder formed at one end of said tubular section thereof which acts as a stop for said tube; and d) a second die mateable with said second punch to transform said crimped end of said tube into a plurality of pleats and form said pleats into a semi-spherically shaped tip having a central aperture formed therethrough, said second die including a base having a semi-spherical cavity formed therein with a central passageway formed at the bottom of said cavity, said cavity being sized to receive both said second punch and said tube and said passageway being sized to receive only said pin.

4. The apparatus of claim 3 wherein said first punch has a configured tip which contains a knurled area which facilitates crimping of said tube when said first punch is brought in contact with said first die.

5. The apparatus of claim 3 wherein said semi-spherically shaped tip formed on said second punch contains a knurled area which facilitates pleating and forming said tube when said second punch is brought in contact with said second die.

6. The apparatus of claim 3 wherein said first die contains at least four blades.

7. The apparatus of claim 3 wherein said first die contains at least eight blades.

8. An apparatus for crimping, pleating and forming a tip on a hollow tube, said apparatus comprising:

a) a first punch having a tubular section sized to receive said tube and a shoulder formed at one end of said tubular section which acts as a stop for said tube, and said first punch further having a smooth tip void of any elongated grooves;

b) a first die mateable with said first punch and tube to crimp an end of said tube, said first die including a base having eight blades extending axially outward therefrom, each of said blades capable of engaging said tube and crimping the tip of said tube positioned between said first die and said first punch;

c) a second punch having a tubular section sized to receive said tube and having a semi-spherically shaped tip with a pin extending outward from the apex thereof, said pin having a circular cross-sectional configuration, and said second punch further having a shoulder formed at one end of said tubular section thereof which acts as a stop for said tube; and d) a second die mateable with said second punch to transform said crimped end of said tube into eight pleats and form said eight pleats into a semi-spherically shaped tip having a central aperture formed therethrough, said second die including a base having a semi-spherical cavity formed therein with a central passageway formed at the bottom of said cavity, said cavity being sized to receive both said second punch and said tube and said passageway being sized to receive only said pin.

9. The apparatus of claim 8 wherein said pin has a diameter of at least 0.062 inches.

10. The apparatus of claim 8 wherein said pin has an essentially constant diameter.

11. The apparatus of claim 8 wherein said pin has a free end and said pin tapers in diameter down from a larger diameter located adjacent to its point of attachment to said tip of said second punch to a smaller diameter at its free end.

12. The apparatus of claim 8 wherein said pin has a length of at least 0.06 inches.

* * * * *